United States Patent [19]

Nomura et al.

[11] Patent Number: 4,650,791
[45] Date of Patent: Mar. 17, 1987

[54] CERTAIN 3-ALKOXY-2-CYCLIC-IMIDO-PROPYL-PHOSPHATE-ETHYL-CYCLIC AMMONIUM HYDROXIDE INNER SALTS WHICH INHIBIT ACTIVITIES OF PLATELET ACTIVATING FACTOR

[75] Inventors: Hiroaki Nomura, Osaka; Kohei Nishikawa, Kyoto; Susumu Tsushima, Osaka, all of Japan

[73] Assignee: Takedo Chemical Industries, Ltd., Osaka, Japan

[21] Appl. No.: 689,730

[22] Filed: Jan. 8, 1985

[30] Foreign Application Priority Data

Jan. 11, 1984 [JP] Japan ................................. 59-4030
Dec. 24, 1984 [JP] Japan ............................. 59-280387

[51] Int. Cl.$^4$ ............... A61K 31/50; A61K 31/535; A61K 31/44; A61K 31/425
[52] U.S. Cl. ........................................ 514/82; 514/85; 514/89; 514/90; 514/92; 546/22; 546/23; 544/157; 544/232; 544/141; 544/144; 548/112; 548/413; 548/415
[58] Field of Search .................. 546/22, 23; 548/112, 548/413, 415; 544/141, 144, 143, 157, 232; 514/90, 82, 85, 89, 92

[56] References Cited

U.S. PATENT DOCUMENTS 4,408,052 10/1983 Hozumi et al. ...................... 546/22
4,426,525 1/1984 Hozumi et al. ...................... 546/22
4,542,219 9/1985 Hozumi et al. ...................... 546/22
4,551,532 11/1985 Hozumi et al. ...................... 546/22
4,565,865 1/1986 Hozumi et al. ...................... 544/110

FOREIGN PATENT DOCUMENTS 58-35116 3/1983 Japan ................................... 546/22

OTHER PUBLICATIONS

Life Sciences, 32, 1975 (1983).
J. Org. Chem., 48, 1197 (1983).
Central Patents Index, Basic Abstracts Journal, Sec. B:FARMDOC 33708 K/14 B03 TAKE 25.08.81, J58035–116.
Biochemical and Biophysical Research Communications, 122, 824–830 (1984).

*Primary Examiner*—Alan L. Rotman
*Attorney, Agent, or Firm*—Wegner & Bretschneider

[57] ABSTRACT

A novel phospholipid of the formula:

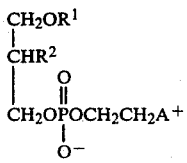

wherein $R^1$ is an alkyl group of 10 to 24 carbon atoms, $R^2$ is a cyclic imide group and $A^+$ is a cyclic ammonio group and a salt thereof have platelet activating factor inhibiting activity and are useful for prevention and treatment of circulatory disorders and allergic bronchial asthma.

13 Claims, No Drawings

CERTAIN 3-ALKOXY-2-CYCLIC-IMIDO-PROPYL-PHOSPHATE-ETHYL-CYCLIC AMMONIUM HYDROXIDE INNER SALTS WHICH INHIBIT ACTIVITIES OF PLATELET ACTIVATING FACTOR

This invention relates to a new platelet activating factor inhibitor. More particularly, this invention relates to a phospholipid of the formula:

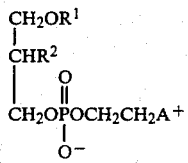

$$\begin{array}{l} CH_2OR^1 \\ | \\ CHR^2 \\ | \quad O \\ | \quad \| \\ CH_2OPOCH_2CH_2A^+ \\ | \\ O^- \end{array} \quad (I)$$

[wherein $R^1$ is an alkyl group of 10 to 24 carbon atoms; $R^2$ is a cyclic imido group; and $A^+$ is a cyclic ammonio group] or a salt thereof. The platelet aggregation has been considered to be a cause of many diseases and, therefore, inhibitors of platelet aggregation constitute an important category of drugs.

The representative substances hitherto known to induce aggregation of platelets are adenosine diphosphate (ADP) and metabolites of arachidonic acid, the latter represented by thromboxane $A_2$ ($TXA_2$). Therefore, platelet aggregation inhibitors have heretofore been selected primarily by a screening method using the inhibition of activity of these compounds as an indicator.

Recently, however, platelet activating factor (PAF) has been discovered as a substance causing platelet aggregation through a mechanism different from that of ADP and $TXA_2$, and the structure of PAF has been identified as 1-O-alkyl-2-acetyl-sn-glyceryl-3-phosphocholine [Nature 285, 193, 1980]. It has been found that PAF displays activity via a mechanism different from that of ADP and $TAX_2$ and in lower concentrations. Moreover, PAF is a potent chemical transmitter of allergy, and it is known that in an assay using bronchoconstriction as an indicator, it has the highest activity among all the known compounds [European Journal of Pharmacology 65, 185–192, 1980]. Therefore, if one could discover a compound having PAF inhibitory activity, it could be of value as a useful inhibitor of platelet aggregation in vivo and also as an effective drug for allergy and other PAF-induced diseases.

Moreover, PAF has strong hypotensive activity in addition to platelet aggregating activity and has been suspected to act as a shock inducer [European Journal of Pharmacology, 86, 403–413, 1983]. Shock is induced by various causes. They may be traumatic, hemorrhagic, cardiogenic, bacteriologic and so forth. However, the pathological condition of shock is almost the same irrespective of causes; thus, circulatory disorders such as hypotension, decreased cardiac output, etc. and metabolic disorders such as metabolic acidosis, hyperpotassemia, lactacidemia, etc. are observed. Taking bacterial shock as an example, it is most often caused by infection of gram-negative rod bacteria (*Escherichia coli*, Pseudomonas sp., Krebsiella sp., etc.), and the causative agent is considered to be the endotoxin which is a cell wall constituent of such microorganisms. Actually, injection of the endotoxin into animals induces shock symptoms. Despite the progress made in antibiotics and transfusion therapy, the high mortality due to shock has not been corrected. Therefore, when a shock is predicted, a drug for preventing endotoxin shock is generally administered in combination with antibiotics. For this purpose, adrenocortical hormones such as hydrocortisone and dexamethasone have been commonly employed but since they are used in massive doses in cases of shock, the onset of side effects of adrenocorticoids presents a clinical problem. Antiinflammatory drugs such as indomethacin have also been utilized but these drugs not only cause side effects such as ulceration but also fail to show a clear-cut efficacy.

The present inventors explored the possible methods for inhibiting the activity of PAF involved in various cardiovascular diseases and shock and found that the compounds represented by formula (I) have potent anti-PAF activity. This invention is predicated on the above finding.

Referring to the above formula (I), the $C_{10-24}$ alkyl group represented by $R^1$ may be straight or branched and includes, among others, decyl, dodecyl, tridecyl, tetradecyl, pentadecyl, hexadecyl, heptadecyl, octadecyl, nonadecyl, eicosanyl, docosanyl, farnesyl and dihydrophthyl. Preferred among them are $C_{14-20}$ alkyl groups.

The cyclic imido group represented by $R^2$ includes phthalimido, succinimido and maleimido, among others. Such cyclic imido group may be substituted, for example, by a lower ($C_{1-4}$)alkyl group such as methyl, ethyl, propyl, isopropyl, butyl or isobutyl, a lower ($C_{1-4}$)alkoxy group such as methoxy or ethoxy, a halogen atom such as chlorine or bromine, a nitro group, a $C_{1-4}$ alkylcarbonyl group such as an acetyl group, etc.

The cyclic ammonio group represented by $A^+$ includes, for example, pyridinio, oxazolio, thiazolio, isothiazolio, pyridazinio, quinolinio, isoquinolinio, N—$C_{1-4}$alkyl-morpholino (e.g. N-methylmorpholinio), N—$C_{1-4}$alkyl-piperidinio (e.g. N-methylpiperidinio) and N—$C_{1-4}$alkyl-pyrrolidinio (e.g. N-methylpyrrolidinio).

The compound (I) may exist in the form of pharmaceutically acceptable salts such as those represented by formulas (Ia) and (Ib):

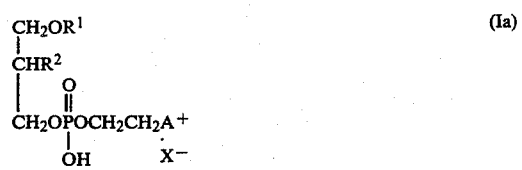

$$\begin{array}{l} CH_2OR^1 \\ | \\ CHR^2 \\ | \quad O \\ | \quad \| \\ CH_2OPOCH_2CH_2A^+ \\ | \\ OH \quad X^- \end{array} \quad (Ia)$$

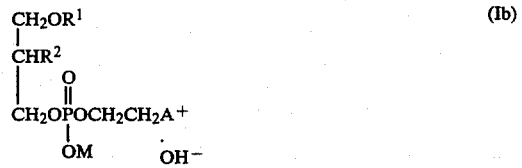

$$\begin{array}{l} CH_2OR^1 \\ | \\ CHR^2 \\ | \quad O \\ | \quad \| \\ CH_2OPOCH_2CH_2A^+ \\ | \\ OM \quad OH^- \end{array} \quad (Ib)$$

[wherein $X^-$ means an anion (e.g. $Cl^-$, $Br^-$, $I^-$, $OH^-$, $CO_3^{2-}$, $SO_4^{2-}$); M means an alkali metal (e.g. Na, K) or alkaline earth metal (e.g Ca); and other symbols have the meanings defined hereinbefore].

Referring to compound (I), it may occur as diastereomers in R- and S-configurations with respect to carbon at position-2 of the propane moiety and each of these two diastereomers as well as a racemic mixture thereof falls within the scope of this invention.

The compound (I) inclusive of salts thereof has excellent platelet activating factor (PAF) inhibiting activity and, more specifically, markedly inhibits PAF-associated platelet aggregation, shock (hypotension, death, etc.) and allergy. Therefore, compound (I) inclusive of its salts can be used in the prophylaxis and treatment of circulatory disorders such as thrombosis, cerebral apoplexy (e.g. cerebral hemorrhage, cerebral thrombosis), myocardial infarction, angina pectoris, thrombotic phlebitis, glomerular nephritis, shock (e.g. endotoxin shock, endotoxin-associated intravascular hemagglutination syndrome, anaphylactic shock), allergic bronchial asthma and other diseases.

The compound (I) inclusive of its salts is so hydrophilic and lipophilic and of such low toxicity that it can be safely administered orally or parenterally as it is in a powdery form or in admixture with other pharmaceutical components in suitable dosage forms. The dosage depends on the subject, symptoms, route of administration, etc. but when the drug is used for the prevention or treatment of thrombosis in adult humans, for instance, it can be advantageously administered in the dose of about 0.1 to 20 mg/kg body weight as compound (I) at the frequency of about once to 3 times a day. More specifically, for the prophylaxis of thrombosis, about 0.5 to 4 mg/kg body weight as compound (I) is usually administered per dose, and for therapeutic purposes, about 4 to 10 mg/kg body weight as compound (I) is usually administered per dose, both at the frequency of about once to 3 times a day.

For the prevention and treatment of shock, the intravenous regimen for adults, for instance, is usually about 0.1 to 20 mg/kg body weight as compound (I) per dose, preferably about 1 to 10 mg/kg body weight, at the frequency of about once to 3 times a day. The compound (I) can also be administered by drip injection in the dose of 0.07 to 0.7 mg/kg body weight/min. over a period of about 1 hour at the frequency of about once to 3 times a day. The dosages for other non-oral routes as well as the oral dosage may be selected referring to the above-mentioned dose levels. When shock symptoms are very serious, dosage increases may be made according to the severity of symptoms.

The compositions used for administration in the above manner contain pharmaceutically acceptable carriers or excipients in addition to the effective amount of compound (I) or salt thereof. Such compositions are supplied in dosage forms suitable for oral, parenteral or other routes of administration.

For example, compositions for oral administration may be solid or liquid, and include tablets (sugar-coated tablets, film-coated tablets, etc.), pills, granules, powders, capsules (inclusive of soft capsules), syrups, emulsions, suspensions, etc. These compositions are manufactured by the established pharmaceutical procedures and contain those vehicles, carriers and/or excipients which are commonly used in the pharmaceutical industry. By way of illustration, the carriers and excipients for tablets may be lactose, starch, sucrose, magnesium, stearate, etc.

The compositions for non-oral administration include injections and suppositories, and such injections include various dosage forms such as intravenous, subcutaneous, intracutaneous, intramuscular and drip injections. Such injections can be manufactured by dissolving, suspending or emulsifying compound (I) or a salt thereof in a sterile aqueous or oily medium which is commonly used in injectable preparations. The aqueous medium for injections includes physiological saline solution, isotonic solutions containing glucose or/and other adjuvants, etc., and may also contain a suitable solubilizing agent such as alcohol (e.g. ethanol), polyalcohol (e.g. propylene glycol, polyethylene glycol), nonionic surfactant (e.g. Polysorbate 80, HCO-50 (polyoxyethylene (50 mol) adduct of hydrogenated castor oil), etc. The oily medium includes, among others, sesame oil and soybean oil. The solubilizing agent may be benzyl benzoate, benzyl alcohol or the like. The injectionable compositions thus prepared are generally filled into suitable ampules. The suppositories for intrarectal administration can be manufactured by incorporating compound (I) or a salt thereof in a suppository base which is per se known.

The above pharmaceutical compositions for oral, parenteral or other routes of administration are conveniently provided in unit dosage forms commensurate with each dose of the active component. Such unit dosage forms include tablets, pills, capsules, ampules, suppositories, etc., and usually each of such dosage form units preferably contains 5 to 500 mg of compound (I), or 5 to 100 mg in the case of injections and 10 to 250 mg in the case of other dosage forms.

It should be understood that the aforesaid compositions may further contain other active components unless untoward interactions with compound (I) are likely.

The compound (I) can be produced for example by the following process.

Process A

A compound of the formula:

(II)

[wherein Y means halogen such as Cl, Br or I; and other symbols have the meanings given hereinbefore] is reacted with a cyclic amine compound A (III) corresponding to A+ to give the compound (I).

Process B

A compound of the formula:

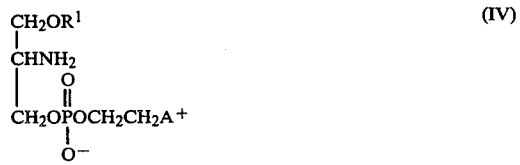

(IV)

[wherein all the symbols have the meanings defined hereinbefore] is reacted with an active derivative of a cyclic imide which may optionally be substituted to give the compound (I).

Process C

A compound of the formula:

$$\begin{array}{c} \text{CH}_2\text{OR}^1 \\ | \\ \text{CHR}^2 \\ | \quad\quad \text{O} \quad \text{X}' \\ \quad\quad \| \diagup \\ \text{CH}_2\text{OP} \\ \quad\quad \diagdown \text{X}' \end{array} \quad (V)$$

[wherein X' means halogen such as Cl or Br; and other symbols have the meanings defined hereinbefore] is reacted with a compound of the formula:

$$\text{HOCH}_2\text{CH}_2\text{A}^+ \cdot \text{X}^- \quad (VI)$$

[wherein $X^-$ means an anion, and other symbols have the meanings defined hereinbefore] to give the compound (I).

Examples of compound (III) used in the above Process A include pyridine, thiazole, oxazole, quinoline, isoquinoline, isothiazole, pyridazine, N-methylmorpholine, N-methyl-piperidine N-methylpyrrolidine, etc. The reaction is conducted by reacting an equivalent to a large excess (e.g. 50 molar equivalents) of base (III) with each mole of compound (II) in the presence or absence of a solvent at room temperature or under heating. The solvent may for example be methanol, toluene, benzene, ether, dioxane or tetrahydrofuran.

The reactive derivative of cyclic imide which may be substituted, which is used in Process B, includes N-ethoxycarbonylphthalimide, N-methoxycarbonylphthalimide, N-ethoxycarbonylsuccinimide, N-ethoxycarbonylmaleimide, etc. The reaction between compound (IV) and such reactive derivative can be carried out under the conditions commonly employed in the reaction of amino compounds with such reactive derivatives. To hasten the reaction, it may also be conducted in the presence of a base such as triethylamine or pyridine.

The reaction according to Process C can be accomplished by reacting 1 to about 1.5 molar equivalents of compound (VI) with compound (V) in the presence of a solvent (e.g. chloroform, dichloromethane, pyridine, toluene, dioxane) at a temperature of 0° to 100° C.

In each of the production processes described above, the time-course of reaction can be traced by thin layer chromatography and the proper reaction conditions can be chosen by such a procedure. The compound obtainable by the above processes can be purified by the conventional procedures such as solvent extraction, recrystallization, chromatography and so forth.

The starting compound (II) can be produced, for example, by reacting a compound of the formula:

$$\begin{array}{c} \text{CH}_2\text{OR}^1 \\ | \\ \text{CHR}^2 \\ | \\ \text{CH}_2\text{OH} \end{array} \quad (VII)$$

[wherein all the symbols have the meanings defined hereinbefore] with a compound of the formula:

$$\begin{array}{c} \text{Z} \quad \text{O} \\ \diagdown \| \\ \text{P}-\text{OCH}_2\text{CH}_2\text{Y} \\ \diagup \\ \text{Z} \end{array} \quad (VIII)$$

[wherein Z is halogen such as chlorine, bromine or iodine, and Y has the meaning defined hereinbefore], followed by hydrolysis.

The compound (II) can be also produced by reacting a reactive derivative of a compound of the formula:

$$\begin{array}{c} \text{HO} \quad \text{O} \\ \diagdown \| \\ \text{P}-\text{OCH}_2\text{CH}_2\text{Y} \\ \diagup \\ \text{HO} \end{array} \quad (IX)$$

[wherein Y has the meaning defined hereinbefore] with the compound (VII). The conversion of the compound (IX) into the reactive derivative can be conducted by per se known methods, such as a method of reacting the compound with phosphorus pentachloride to provide a phosphoryl chloride thereof, or a method of activating the compound with a per se known reagent such as 2,4,6-trimethylbenzenesulfonyl chloride, 8-quinolinesulfonyl chloride, 2,4,6-isopropylbenzenesulfonyl imidazolide 2,4,6-trimethylbenzenesulfonyl tetrazolide or dicyclohexylcarbodiimide.

The compound (VII) can be produced, for example, by the following methods.

(a) A compound of the formula:

$$\begin{array}{c} \text{CH}_2\text{OR}^1 \\ | \\ \text{CHNH}_2 \\ | \\ \text{CH}_2\text{OH} \end{array} \quad (X)$$

[wherein $R^1$ has the meaning defined hereinbefore] is reacted with a compound of the formula:

$$R^2\text{—COOR}^3 \quad (XI)$$

[wherein $R^3$ is lower ($C_{1-4}$)alkyl such as methyl or ethyl and $R^2$ has the meaning defined hereinbefore] to provide the compound (VII). The starting compound (X) can be produced, for example, by applying the method as described in the literature reference [Hajdu et al., J. Org. Chem. 48, 1197–1202 (1983)] with use of serin as a starting material, according to the route as follows:

$$\begin{array}{c} \text{COOH} \\ | \\ \text{H}_2\text{N}-\text{CH} \\ | \\ \text{CH}_2\text{OH} \end{array} \xrightarrow[\text{(ii) PhC}\diagdown_{\text{OEt}}^{\diagup \text{NH}}]{\text{(i) HCl/MeOH}}$$

$$\begin{array}{c} \text{N} \quad\quad \text{COOMe} \\ \diagup\!\!\!\!\| \quad \diagup \\ \text{Ph—C} \quad\quad \\ \diagdown \quad \diagdown \\ \quad\quad \text{O} \end{array} \xrightarrow{\text{LiAlH}_4}$$

$$\begin{array}{c} \text{N} \quad\quad \text{CH}_2\text{OH} \\ \diagup\!\!\!\!\| \quad \diagup \\ \text{Ph—C} \quad\quad \\ \diagdown \quad \diagdown \\ \quad\quad \text{O} \end{array} \xrightarrow{\text{alkyl halide}}$$

$$\begin{array}{c} \text{N} \quad\quad \text{CH}_2\text{OR}^1 \\ \diagup\!\!\!\!\| \quad \diagup \\ \text{Ph—C} \quad\quad \\ \diagdown \quad \diagdown \\ \quad\quad \text{O} \end{array} \xrightarrow[\text{(ii) aq. K}_2\text{CO}_3]{\text{(i) H}_2\text{SO}_4} (X)$$

[wherein Ph is phenyl, Me is methyl and Et is ethyl]

(b) A compound of the formula:

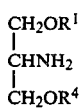
(XII)

[wherein $R^1$ has the meaning defined hereinbefore, and $R^4$ is a protective group] with an anhydride or dicarboxylic acid such as phthalic anhydride, maleic anhydride or succinic anhydride, followed by activating the carboxyl group and cyclization to give a compound of the formula:

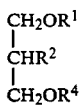
(XIII)

[wherein $R^1$ and $R^4$ are the meanings defined hereinbefore]. The deprotection reaction is conducted to give the compound (VII). In the above-mentioned reaction, a reagent for activating the carboxyl group includes, for example, acetic anhydride and a base, dicyclohexylcarbodiimide and oxalyl chloride. The starting compound (XII) can be produced, for example, by the following method.

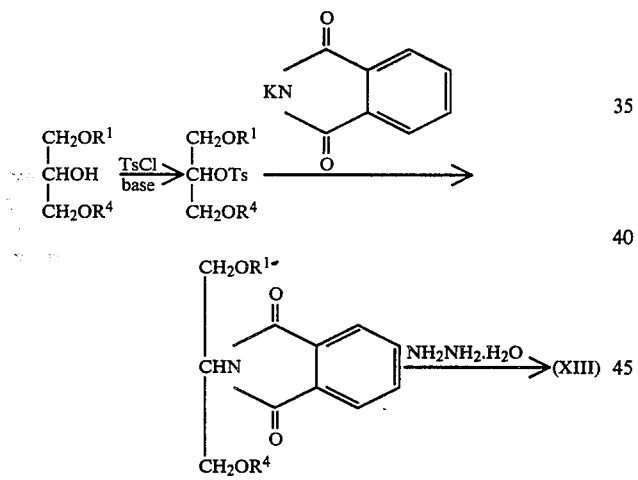

[wherein Ts is tosyl]

(c) The compound (XIII) is reacted with an acid halide such as succinyl chloride, maleoyl chloride or phthaloyl chloride, and the obtained compound (XIII) is subjected to deprotection reaction to give the compound (VII).

(d) A compound of the formula:

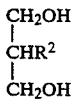
(XIV)

[wherein $R^2$ has the meaning defined hereinbefore] is reacted with an alkyl halide to give the compound (VII). The compound (XIV) can be produced, for example, by the following method with use of serin.

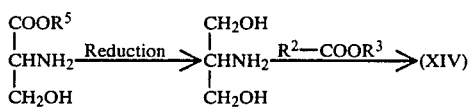

[wherein $R^2$ and $R^3$ have the meanings defined hereinbefore and $R^5$ is methyl or ethyl]

(e) A compound of the formula:

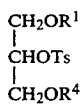
(XV)

[wherein $R^1$ and $R^4$ have the meanings defined hereinbefore and Ts is tosyl] is reacted with an optionally substituted cyclic imide compound or an alkali metal (e.g. K) salt thereof, followed by deprotection reaction to give the compound (VII).

In the above-mentioned methods (b), (c) and (e), the protective group represented by $R^4$ includes per se known protective groups for primary alcohols, such as trityl, benzyl or tetrahydropyranyl.

The representative methods for producing the compound (VII) are shown hereinbefore, but they should by no means be limitative of the methods for producing the compound (VII).

The compound (VII) obtainable by the above processes can be purified by the conventional procedures such as solvent extraction, recrystallization, chromatography and so forth, but it can be used for a process for producing the compound (I) without such a purification.

This invention also provides the compound (VII) which is useful as an intermediate for producing the compound (I).

The starting compound (IV) can be produced, for example, by subjecting a compound of the formula:

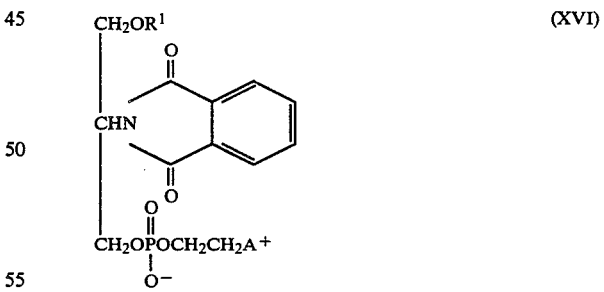
(XVI)

[wherein $R^1$ and $A^+$ have the meanings defined hereinbefore] to deprotection reaction using hydrazine hydrate. The compound (XVI) can be produced, for example, according to Process A.

The starting compound (V) can be produced, for example, by reacting the compound (VII) with phosphorus oxide trihalide such as phosphorus oxychloride.

The following examples, inclusive of test examples and dosage form examples, are intended to illustrate this invention in further detail and should by no means be limitative of the scope of the invention.

EXAMPLE 1

3-O-Octadecyl-2-O-tosyl-1-O-tritylglycerol

In 9 ml of pyridine was dissolved 5.0 g (8.52 millimoles) of 3-O-octadecyl-1-O-tritylglycerol, and 1.95 g (10.22 millimoles) of tosyl chloride was added to the solution. The mixture was stirred at room temperature overnight and concentrated to dryness under reduced pressure. The residue was dissolved in 50 ml of water and 50 ml of dichloromethane and, after shaking, the dichloromethane layer was separated. The organic layer was concentrated to dryness under reduced pressure and the residue was purified by silica gel (50 g) column chromatography using n-hexaneethyl acetate (193:7) as an eluent to give 5.3 g (83.9%) of colorless needles.

M.p. 52° C.–53° C.

EXAMPLE 2

3-Octadecyloxy-2-phthalimido-1-trityloxypropane

In 53 ml of dimethyl sulfoxide was dissolved 5.3 g (7.15 millimoles) of the tosyl compound as obtained in Example 1, and 10.6 g of potassium phthalimide was added to the solution. The mixture was stirred in a bath at 115° C. for 3.5 hours, poured into 500 ml of water and extracted with 500 ml of ether. The ether layer was dried over sodium sulfate and concentrated to dryness under reduced pressure. The residue was purified by silica gel (50 g) column chromatography using n-hexane-ethyl acetate (193:7) as an eluent to give 3.0 g (58.6%) of a colorless oil.

TLC[silica gel, n-Hexane, EtOAc (9:1)] Rf=0.25 single spot.

EXAMPLE 3

1-Hydroxy-3-octacdecyloxy-2-phthalimidopropane

In 50 ml of 70% acetic acid was dissolved 3.0 g (4.19 millimoles) of the trityl compound as obtained in Example 2, and the solution was refluxed for 1 hour. The reaction mixture was concentrated to dryness under reduced pressure and the residue was purified by silica gel (40 g) column chromatography using n-hexane-ethyl acetate (4:1) as an eluent to give 1.17 g (58.9%) of colorless needles.

M.p. 60° C.–61° C.

TLC[silica gel, n-Hexane, EtOAc (4:1)] Rf=0.16

IR(KBr)cm$^{-1}$: 3500, 3450, 2910, 2850, 1765, 1700, 1465, 1390, 1150, 1060, 875.

EXAMPLE 4

3-Octadecyloxy-2-phthalimidopropyl 2-bromoethyl phosphate

In 8 ml of benzene was dissolved 1.894 g (4 millimoles) of the hydroxy compound as obtained in Example 3, and 1.45 g (6 millimoles) of 2-bromoethyl phosphorodichloridate and 0.475 g (6 millimoles) of pyridine were added dropwise to the solution. The mixture was stirred at room temperature for 4 hours and then concentrated to dryness under reduced pressure. The residue was transferred into 100 ml of water and the mixture was heated at 50° C. for 30 minutes while maintaining the pH at 7.0, followed by refluxing for 30 minutes. After cooling, the mixture was extracted with 60 ml of ether and the ether layer was concentrated to dryness under reduced pressure to give 2.64 g (100%) of a colorless solid.

EXAMPLE 5

3-Octadecyloxy-2-phthalimidopropyl 2-pyridinioethyl phosphate

In 20 ml of pyridine was dissolved 2.27 g (3.55 millimoles) of the bromide as obtained in Example 4 and the solution was heated in a water bath at 60° C. for 2 days. The reaction mixture waas concentrated under reduced pressure and the residue was purified with silica gel (20 g) column chromatography using methanol as an eluent to give 740 mg (33.3%) of a light-brown solid.

TLC[silica gel, CHCl$_3$, MeOH, H$_2$O (65:25:4)] Rf=0.21 single spot.

IR(film)cm$^{-1}$: 3400, 2930, 2850, 1775, 1710, 1635, 1490, 1465, 1395, 1250, 1100, 1075, 1050, 760, 720. p NMR(60MC, CDCl$_3$)δ: 0.88(3H), 1.27(32H), 3.40(2H), 3.80(2H), 4.22(4H), 4.60(1H), 4.73(2H), 7.72(4H), 8.07(2H), 8.42(1H), 9.08(1H).

EXAMPLE 6

3-Octadecyloxy-2-phthalimidopropyl 2-thiazolioethyl phosphate

In a mixture of thioazole (5 ml) and toluene (5 ml) was dissolved 2.27 g of the bromide as obtained in Example 4, and the whole mixture was heated at 65° C. for 7 hours and then concentrated to dryness under reduced pressure. The residue was purified by silica gel column chromatography to give 540 mg of the contemplated compound.

TLC[silica gel, CHCl$_3$, MeOH, H$_2$O (65:25:4)] Rf=0.22

EXAMPLE 7

3-Octadecyloxy-2-amino-1-trityloxypropane

In 50 ml of isopropylalcohol was dissolved 6.4 g of 3-octadecyloxy-2-phthalimido-1-trityloxypropane, and 4 ml of hydrazine hydrate was added to the solution. The mixture was heated at 70° C. for 1 hour, and concentrated under reduced pressure. Ethyl acetate was added to the residue and the insoluble matter was filtered off. The filtrate was concentrated to dryness and purified by silica gel chromatography (eluent: n-hexane-ethyl acetate=3:1) to give 4.41 g (84%) of the desired compound as a pale brown solid.

NMR(90 MHz, CDCl$_3$)δ: 0.87(3H, t), 1.25(32H, m), 3.0–3.56(7H, m), 7.2–7.5(15H, m).

EXAMPLE 8

3-Octadecyloxy-2-(2-carboxyethylcarbonylamino)-1-trityloxypropane

In 10 ml of chloroform was dissolved 2.34 g (4 mmoles) of 2-aminopropane derivative obtained in Example 7, and 2 ml of triethylamine and 0.48 g (4.8 mmoles) of succinic anhydride were added to the solution. The mixture was refluxed overnight, concentrated to dryness and purified by silica gel chromatography (eluent: chloroform-methanol=20:1) to give 2.33 g (85%) of a pale brown solid.

IR(KBr, cm$^{-1}$): 3265, 3060, 2925, 2850, 1730, 1680, 1648, 1550, 1490, 1470, 1455, 1400, 1255, 1088, 1020, 705.

NMR(90 MHz, CDCl$_3$)δ: 0.87(3H, t), 1.25(32H, s), 2.25–2.75(4H, m), 3.0–3.75(6H, m) 4.22(1H, m), 5.95(1H, d) 7.15–7.50(15 H, m).

EXAMPLE 9

3-Octadecyloxy-2-succinimodopropanol

A mixture of 2.21 g of the carboxyl compound obtained in Example 8 and 0.45 g of sodium acetate in 10 ml of acetic anhydride was heated at 100° C. for 2 hours, and the mixture was concentrated under reduced pressure. n-Hexane was added to the mixture and the insoluble matter was filtered off. The filtrate was concentrated to dryness to give a crude product of 3-octadecyloxy-2-succinimido-1-trityloxypropanol. This crude trityl compound in 20 ml of 70% acetic acid was heated at 100° C. for 2 hours. The reaction mixture was concentrated to dryness and the residue was purified by silica gel chromatography (chloroform-methanol=20:1) to give 1.316 g (95%) of the desired compound as a colorless powder.

IR(KBr, cm$^{-1}$): 3525, 2970, 2925, 2850, 1768, 1698, 1470, 1392, 1180, 1122, 1060, 725.

NMR(90 MHz, CDCl$_3$)δ: 0.87(3H, t), 1.25(32H, m), 2.71(4H, s), 2.9(1H, br), 3.40(2H, m), 3.65–4.0(4H, m), 4.48(1H, m).

m.p. 76°–78° C.

EXAMPLE 10

3-Octadecyloxy-2-succinimidopropanol

A mixture of 3.43 g (10 mmoles) of 3-octadecyloxy-2-aminopropanol synthesized according to the method of J. Hajdu et al. [J. Org. Chem., 48, 1197–1202 (1983)] and 1.73 g (10 mmoles) of carboethoxysuccinimide in 50 ml of dichloromethane was stirred, and 1.01 g of triethylamine was added to the mixture under ice-cooling. The resulting mixture was stirred at room temperature for 30 hours and concentrated to dryness. The residue was purified by silica gel chromatography to give 894 mg of the desired 2-succinimidopropane derivative.

The spectral data of this compound were identical with those of the compound obtained in Example 9.

EXAMPLE 11

3-Octadecyloxy-2-succinimidopropyl 2-bromoethyl phosphate

In 20 ml of toluene was dissolved 638 mg (1.5 mmoles) of 3-octadecyloxy-2-succinimidopropanol, and 786 mg (3.25 mmoles) of bromoethyl phosphorodichloridate and 101 mg (3.25 mmoles) of triethylamine were added to the solution under cooling. The mixture was stirred at room temperature for 4 hours, and, then, 20 ml of water and 0.5 ml of conc. hydrochloric acid were added to the mixture. After the resulting mixture was stirred at 80° C. for 1 hour, the solvent was evaporated off. The residue was dissolved in ether, washed with water, concentrated and dried to give 939 mg of the desired bromide compound.

EXAMPLE 12

3-Octadecyloxy-2-succinimidopropyl 2-thiazolioethyl phosphate

In 1 ml of thiazole was dissolved 0.30 g of the crude bromide compound obtained in Example 11, and the mixture was heated at 80° C. for 26 hours. The mixture was concentrated to dryness and the residue was purified by silica gel chromatography [eluent: (i) methanol (ii) chloroform-methanol-water=65:25:4] to give 121 mg of the desired compound as a colorless solid.

IR(KBr, cm$^{-1}$): 3410, 2850, 1775, 1550, 1470, 1400, 1240, 1200, 1065, 830.

NMR(90 MHz, CDCl$_3$)δ: 0.87(3H, t), 1.25(32H, m), 2.69(4H, s), 3.2–3.5(2H, m), 3.5–4.05(4H, m), 4.2(2H, br), 4.5(1H, m), 4.83(2H, m), 8.20(1H), 8.49(1H), 10.4(1H).

TLC: Rf=0.24 (chloroform-methanol-water=65:25:4).

EXAMPLE 13

3-Octadecyloxy-2-maleimidopropanol

In 5 ml of dichloromethane were dissolved 495 mg (5 mmoles) of ethyl chloroformate in 5 ml of dichloromethane was added dropwise to the solution under ice-cooling. After the mixture was stirred at room temperature for 1 hour, 1.37 g (4 mmoles) of 3-octadecyloxy-2-aminopropanol, 10 ml of dichloromethane and 0.55 ml (4 mmoles) of triethylamine were added to the mixture. The reaction mixture was stirred at room temperature and concentrated to dryness. The residue was purified by silica gel chromatography (eluent: n-hexane-ethyl acetate=3:1) and recrystallized from n-hexane to give 675 mg of the desired product as colorless needles.

IR(KBr, cm$^{-1}$): 3548, 2960, 2925, 2852, 1768, 1700, 1498, 1470, 1408, 1390, 1120, 1058, 830, 770.

NMR(90 MHz, CDCl$_3$)δ: 0.87(3H, t), 1.25(32H, br-s), 2.51(1H, OH), 3.39(2H, m), 3.73(2H, d), 3.92(2H, t), 4.41(1H, m), 6.68(2H, s, maleimide).

TLC Rf=0.17 (n-hexane-ethyl acetate=3:1).

m.p. 58°–60° C.

EXAMPLE 14

3-Octadecyloxy-2-maleimidopropyl 2-thiazolioethyl phosphate

Using 634 mg of 3-octadecyloxy-2-maleimidopropanol obtaned in Example 13 and 544 mg of 2-bromoethyl phosphorodichloridate, the reaction was conducted in the same manner as that described in Examples 11 and 12 to give the desired product.

NMR(CDCl$_3$)δ: 0.87(3H, t), 1.25(32H, m), 3.2–4.0(6H, m), 4.2(2H, m), 4.4(1H, m), 4.8(2H, m), 6.7(2H, s), 8.2, 8.5, 10.4(3H, thiazolio).

IR(KBr, cm$^{-1}$): 2925, 2850, 1772, 1702, 1550, 1470, 1240, 1065.

In the same manner as Examples, there were synthesized the following compounds:

3-Hexadecyloxy-2-phthalimido-1-propanol;
3-Octadecyloxy-2-succinimidopropyl 2-pyridinioethyl phosphate;
3-Octadecyloxy-2-maleimidopropyl 2-pyridinioethyl phosphate;
3-Hexadecyloxy-2-phthalimidopropyl 2-pyridinioethyl phosphate;
3-Hexadecyloxy-2-phthalimidopropyl 2-thiazolioethyl phosphate;
3-Octadecyloxy-2-phthalimidopropyl 2-isoquinolinioethyl phosphate;
3-Octadecyloxy-2-phthalimidopropyl 2-quinolinioethyl phosphate;
3-Octadecyloxy-2-phthalimidopropyl 2-(N-methylpyrrolidinio)ethyl phosphate; and
3-Octadecyloxy-2-phthalimidopropyl 2-(N-methylpiperidinio)ethyl phosphate.

TEST EXAMPLE 1

PAF-inhibiting activity

Activity to inhibit PAF in platelet aggregation
[Method and result]

Using an injection syringe containing a 3.15% solution of citric acid (in a ratio of 1 part per 9 parts of blood) as an anticoagulant, the blood was directly collected from a male rabbit. Then, at room temperature, the blood was centrifuged at 1,000 r.p.m. for 10 minutes to harvest a platelet rich plasm (PRP). This PRP was further centrifuged at 1,400 r.p.m. for 15 minutes to give platelet pellets. The pellets were suspended in $Ca^{++}$-free Tyrode solution (containing 0.25% of gelatin) to give a washed PRP. This washed PRP (250 μl) was stirred at 37° C. for 2 minutes, then 25 μl of a 0.2 to 0.5 mM $Ca^{++}$ solution was added, and the mixture was further stirred for 30 seconds. Then, the compound obtained in Example 5 was added to a concentration of $3 \times 10^{-5}$M. After stirring the mixture for 2 minutes, $3 \times 10^{-5}$M of PAF was added. The degree of platelet aggregation was determined with a platelet aggregometer (Rika Denki). The activity of the test drug was estimated from the inhibition rate relative to the maximum transmission (maximum aggregation) of control PRP by PAF. The inhibition rate thus found was 70%.

TEST EXAMPLE 2

Activity on inhibiting platelet aggregation
[Method and results]

Using an injection syringe containing 3.15% citric acid (in a ratio of 1 part per 9 parts of blood) as an anticoagulant, the blood was directly collected from a male rabbit. Then, at room temperature, the blood was centrifuged at 800 r.p.m. for 10 minutes to harvest a platelet rich plasma (PRP). The remaining blood was further centrifuged at 3,000 r.p.m. for 10 minutes to separate a platelet poor plasma (PPP) as a supernatant. The PRP was diluted with the PPP to adjust the number of platelets to about 0.5 million ($5 \times 10^5$) per μl. This PRP (250 μl) was stirred at 37° C. for 2 minutes, and the test compound was added to the PRP. After stirring the mixture for 2 minutes, $1 \times 10^{-8}$M of PAF was added to the mixture. The degree of platelet aggregation was determined with a platelet aggregometer (Rika Denki). The aggregation inhibitory activity of the test compound was estimated from the inhibition rate relative to the maximum transmission (maximum aggregation) of control PRP by PAF.

The results are shown in Table 1.

TABLE 1

| Test compound Example No. | Concentration of test compound and Inhibition rate (%) | |
|---|---|---|
| | $3 \times 10^{-6}$ (M) | $3 \times 10^{-5}$ (M) |
| 6 | 96 | 100 |
| 12 | 32 | 100 |

DOSAGE FORM EXAMPLE

In 1.0 l of distilled water is dissolved 10 g of 3-octadecyloxy-2-phthalimidopropyl 2-pyridinioethyl phosphate and, after sterile filtration, the solution is aseptically distributed in 1-ml portions into 1000 vials and lyophilized. Thereafter, the vials are sealed.

On the other hand, 2 l of distilled water for injection containing 100 g of xylitol or mannitol is distributed in 2-ml portions into 1000 injection ampules which are then fusion-sealed.

For administration, one vial equivalent of this powder is dissolved in xylitol (or mannitol) solution for injection.

What we claim is:

1. A compound of the formula:

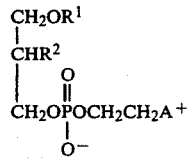

wherein
$R^1$ is an alkyl group of 10 to 24 carbon atoms,
$R^2$ is phthalimido, succinimido or maleimido, each of said groups being unsubstituted or substituted by $C_{1-4}$ alkyl, $C_{1-4}$ alkoxy, halogen, nitro or $C_{1-4}$ alkylcarbonyl, and
$A^+$ is pyridinio, oxazolio, thiazolio, isothiazolio, pyridazinio, quinolinio, isoquinolinio, N—$C_{1-4}$alkylmorpholinio, N—$C_{1-4}$alkylpiperidinio or N—$C_{1-4}$alkylpyrrolidinio, or a pharmaceutically acceptable salt thereof.

2. A compound according to claim 1, wherein $R^1$ is an alkyl group of 14 to 20 carbon atoms.

3. A compound according to claim 1, wherein $R^1$ is octadecyl.

4. A compound according to claim 1, wherein $R^2$ is phthalimido, succinimido or maleimido.

5. A compound according to claim 1, wherein $R^2$ is phthalimido.

6. A compound according to claim 1, wherein $A^+$ is pyridinio, oxazolio, thiazolio, isothiazolio, pyridazinio, quinolinio, isoquinolinio, N-methylmorpholinio, N-methylpiperidinio or N-methylpyrrolidinio.

7. A compound according to claim 1, wherein $A^+$ is pyridinio or thiazolio.

8. The compound according to claim 1, which is 3-octadecyloxy-2-phthalimidopropyl 2-pyridinioethyl phosphate.

9. The compound according to claim 1, which is 3-octadecyloxy-2-phthalimidopropyl 2-thiazolioethyl phosphate.

10. The compound according to claim 1, which is 3-octadecyloxy-2-succinimidopropyl 2-thiazolioethyl phosphate.

11. The compound according to claim 1, which is 3-octadecyloxy-2-maleimidopropyl 2-thiazolioethyl phosphate.

12. A pharmaceutical composition suitable for inhibiting activities of platelet activating factor which comprises, as an active ingredient, an effective amount of a compound of the formula:

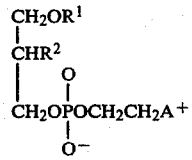

wherein
$R^1$ is an alkyl group of 10 to 24 carbon atoms,
$R^2$ is phthalimido, succinimido or maleimido, each of said groups being unsubstituted or substituted by $C_{1-4}$ alkyl, $C_{1-4}$ alkoxy, halogen, nitro or $C_{1-4}$ alkylcarbonyl, and A+ is pyridinio, oxazolio, thiazolio, isothiazolio, pyridazinio, quinolinio, isoquinolinio, N—$C_{1-4}$alkylmorpholinio, N—$C_{1-4}$alkylpiperidinio or N—$C_{1-4}$alkylpyrrolidinio, or a pharmaceutically acceptable salt thereof, and a pharmaceutically acceptable carrier, excipient or diluent therefor.

13. A method for inhibiting activities of platelet activating factor in a mammal which comprises administering said mammal an effective amount of a compound of the formula:

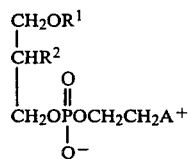

wherein
$R^1$ is an alkyl group of 10 to 24 carbon atoms,
$R^2$ is phthalimido, succinimido or maleimido, each of said groups being unsubstituted or substituted by $C_{1-4}$ alkyl, $C_{1-4}$ alkoxy, halogen, nitro or $C_{1-4}$ alkylcarbonyl, and
A+ is pyridinio, oxazolio, thiazolio, isothiazolio, pyridazinio, quinolinio, isoquinolinio, N—$C_{1-4}$alkylmorpholinio, N—$C_{1-4}$alkylpiperidinio or N—$C_{1-4}$alkylpyrrolidinio, or a pharmaceutically acceptable salt thereof.

* * * * *